(12) United States Patent
Inada et al.

(10) Patent No.: US 6,710,202 B2
(45) Date of Patent: Mar. 23, 2004

(54) PROCESS FOR PRODUCTION OF HIGH-PURITY BIS-β-HYDROXYETHYL TEREPHTHALATE

(75) Inventors: Shuji Inada, Suita (JP); Kikuchi Sato, Fukuyama (JP)

(73) Assignee: Aies Co., Ltd., Osaka (JP)

( * ) Notice: Subject to any disclaimer, the term of this patent is extended or adjusted under 35 U.S.C. 154(b) by 14 days.

(21) Appl. No.: 10/203,234

(22) PCT Filed: Jan. 31, 2001

(86) PCT No.: PCT/JP01/00651

§ 371 (c)(1), (2), (4) Date: Aug. 5, 2002

(87) PCT Pub. No.: WO01/56970

PCT Pub. Date: Aug. 9, 2001

(65) Prior Publication Data

US 2003/0050499 A1 Mar. 13, 2003

(30) Foreign Application Priority Data

Feb. 4, 2000 (JP) ......................................... 2000-026967

(51) Int. Cl.$^7$ ........................ C07C 67/48; C07C 69/76; C07C 67/08; C07C 67/00
(52) U.S. Cl. ........................... 560/78; 560/76; 560/89; 560/96; 560/98
(58) Field of Search ............................ 560/76, 89, 96, 560/98, 78

(56) References Cited

U.S. PATENT DOCUMENTS 3,803,003 A    4/1974   Matsuzawa et al. .......... 560/78

FOREIGN PATENT DOCUMENTS

| GB | 1143072 | 2/1969 |
| JP | A-48-15846 | 2/1973 |
| JP | A-49-36646 | 4/1974 |
| WO | WO 94/26684 | 11/1994 |

OTHER PUBLICATIONS

"Kagaku Binran", Ed. 55, pp. 535 (1992).
Patent Abstracts of Japan: Publication No. JP-A-2000-169623, published on Jun. 20, 2000.
Patent Abstracts of Japan: Publication No. JP-A-2000-159729, published on Jun. 13, 2000.

*Primary Examiner*—Alan L. Rotman
*Assistant Examiner*—Taylor V. Oh
(74) *Attorney, Agent, or Firm*—Anderson Kill & Olick; Eugene Lieberstein; Micheal N. Meller

(57) ABSTRACT

To provide a process for producing a high-purity bis-β-hydroxyethyl terephthalate from crude terephthalic acid.

A process for producing high-purity bis-β-hydroxyethyl terephthalate by carrying out the following steps (1) to (4) in the mentioned order: (1) the step of esterifying crude terephthalic acid with ethylene glycol and/or ethylene oxide to form a reaction product containing bis-β-hydroxyethyl terephthalate, (2) the step of preparing a solution containing bis-β-hydroxyethyl terephthalate as the main solute and ethylene glycol as the main solvent by mixing the above reaction product obtained in the above step (1) with ethylene glycol as required and deionizing the solution to form a deionized solution of bis-β-hydroxyethyl terephthalate, (3) the step of distilling off substances having a boiling point lower than that of bis-β-hydroxyethyl terephthalate from the above deionized solution obtained in the step (2) to form crude bis-β-hydroxyethyl terephthalate, and (4) the step of subjecting the crude bis-β-hydroxyethyl terephthalate obtained in the step (3) to molecular distillation to distill out bis-β-hydroxyethyl terephthalate.

8 Claims, No Drawings

PROCESS FOR PRODUCTION OF HIGH-PURITY BIS-β-HYDROXYETHYL TEREPHTHALATE

FIELD OF THE INVENTION

The present invention relates to a process for producing high-purity bis-β-hydroxyethyl terephthalate from crude terephthalic acid.

DESCRIPTION OF THE PRIOR ART

Bis-β-hydroxyethyl terephthalate is widely used as a raw material for polyethylene terephthalate which is an extremely useful polyester in the field of various moldings such as fibers, films and resins.

Polyesters, particularly polyesters comprising polyethylene terephthalate as the main constituent are widely used for various purposes as described above and mainly produced by obtaining an intermediate containing bis-β-hydroxyethyl terephthalate through direct esterification between terephthalic acid and ethylene glycol or through an ester exchange reaction between a lower alkyl ester of terephthalic acid, especially dimethyl terephthalate, and ethylene glycol and then generally polycondensing the intermediate at a high temperature under a high vacuum. These production processes are currently put to practical use. Due to the recent diversified application of the polyesters based on their excellent properties, requirements for obtaining higher quality are being more and more diversified and advanced. One of the characteristic features of the polyesters is that they can be decomposed into their raw materials which can be polymerized again to obtain new polyesters. Therefore, it can be said that they are excellent in terms of resource saving.

Terephthalic acid as a raw material for terephthalate-based polyesters is generally supplied by oxidizing paraxylene. However, as terephthalic acid obtained by this method has low purity and is colored in most cases, it cannot be used for the production of a polyester as it is. Therefore, it must be purified before it is used for the production of a polyester. However, it is not easy to purify terephthalic acid because of its low solubility in solvents.

That is, terephthalic acid is obtained by air oxidizing paraxylene at about 175 to 230° C. in an acetic acid solvent using a catalyst comprising cobalt, manganese and bromine compounds in accordance with a so-called Amoco process. In this case, paratoluylic acid and 4-carboxybenzaldehyde by-produced in the above oxidation step, metals such as cobalt and manganese used as a catalyst and halogen such as bromine remain in the obtained terephthalic acid, and the existence of a compound such as 3,6-dicarboxyfluorenone as a coloring impurity is also known. Kagaku Binran, Applied Chemistry I, Process, pp. 535 (fifth edition published on Apr. 20, 1992) teaches that high-purity terephthalic acid is obtained by passing a water slurry solution containing 10% or more of the above crude terephthalic acid through a reactor maintained at a temperature of 250° C. or more to purify the crude terephthalic acid by hydrogenation in the above Amoco process. The catalyst used in this case is a precious metal carried on active carbon. It is disclosed that the contents of 4-carboxybenzaldehyde and the coloring component in the formed product thereby become very small. However, as terephthalic acid is generally obtained as a fine particle solid, it is very difficult to handle it. Therefore, it is often supplied as a slurry containing ethylene glycol to an industrial-scale production process. As easily anticipated by people having ordinary skill in the art, it is difficult to remove impurities due to big changes in the properties and reactivity of the slurry caused by non-uniformity in particle diameter.

A process in which terephthalic acid is purified as dimethyl terephthalate which is a functional derivative relatively easy to be purified and a polyester is obtained through an ester exchange reaction between it and ethylene glycol has also been employed. However, in this so-called ester exchange process, it is necessary to recycle methanol which is by-produced inevitably, thereby imposing great restrictions on equipment and handling. In this case, there arises another problem that an ester exchange catalyst is contained in the polyester product. Further, when a polyester obtained by the ester exchange process is molded into a bottle, for example, the bottle is unsatisfactory in terms of color, transparency and moldability.

Such an attempt is also proposed to obtain bis-β-hydroxyethyl terephthalate from terephthalic acid and purify this bis-β-hydroxyethyl terephthalate by distillation.

JP-A 48-15846 (the term "JP-A" as used herein means an "unexamined published Japanese patent application") discloses a process for obtaining high-purity bis-β-hydroxyethyl terephthalate by reacting high-purity terephthalic acid with ethylene oxide in the presence of a basic catalyst to obtain bis-β-hydroxyethyl terephthalate and distilling this bis-β-hydroxyethyl terephthalate at a temperature of 200 to 350° C. under reduced pressure quickly and teaches that when quick distillation is carried out in this process in the presence of a phosphorus, sulfur or boron compound, the polymerization rate of bis-β-hydroxyethyl terephthalate can be controlled and bis-β-hydroxyethyl terephthalate can be obtained at a high yield. However, the results of studies conducted by the present inventor revealed that the purification of bis-β-hydroxyethyl terephthalate containing various impurity ions cannot be realized because these metal compounds separate out on the evaporation surface, thereby greatly preventing heat transmission with the result that long-term continuous stable operation cannot be continued substantially.

JP-A 49-36646 discloses a process for purifying bis-β-hydroxyethyl terephthalate by distillation at a temperature of 140 to 190° C. by maintaining the pressure of an output port at a range of 0.01 to 0.1 mmHg. However, the results of studies conducted by the present inventor revealed that the purification of bis-β-hydroxyethyl terephthalate containing various impurity ions cannot be realized even when this process is carried, because polycondensation takes place with the passage of operation time, thereby making impossible to carry out distillation operation.

SUMMARY OF THE INVENTION

It is an object of the present invention to provide a process for producing high-purity bis-β-hydroxyethyl terephthalate from crude terephthalic acid.

It is another object of the present invention to provide a process for producing high-purity bis-β-hydroxyethyl terephthalate which makes it easy to remove impurities and possible to purity crude terephthalic acid by removing impurities contained in the crude terephthalic acid after terephthalic acid is converted into bis-β-hydroxyethyl terephthalate without purifying the crude terephthalic acid.

Other objects and advantages of the present invention will become obvious from the following description.

According to the present invention, firstly, the above objects and advantages of the present invention are attained by a process for producing high-purity bis-β-hydroxyethyl terephthalate by carrying out the following steps (1) to (4) in the mentioned order:

(1) the step of esterifying crude terephthalic acid with ethylene glycol and/or ethylene oxide to form a reaction product containing bis-β-hydroxyethyl terephthalate;

(2) the step of preparing a solution containing bis-β-hydroxyethyl terephthalate as the main solute and ethylene glycol as the main solvent by mixing the above reaction product obtained in the above step (1) with ethylene glycol as required and deionizing the solution to form a deionized solution of bis-β-hydroxyethyl terephthalate;

(3) the step of distilling off substances having a boiling point lower than that of bis-β-hydroxyethyl terephthalate from the above deionized solution obtained in the step (2) to form crude bis-β-hydroxyethyl terephthalate; and (4) the step of subjecting the crude bis-β-hydroxyethyl terephthalate obtained in the step (3) to molecular distillation to distill out bis-β-hydroxyethyl terephthalate.

The present inventor has paid attention to bis-β-hydroxyethyl terephthalate obtained by the esterification of terephthalic acid and studied a process for purifying this compound. As a result, he has succeeded in reducing the total amount of ions contained in this bis-β-hydroxyethyl terephthalate to an extremely low level by a specific method and purifying it by distillation. The present inventor has found for the first time that it is a very important technical factor to reduce the total amount of ions contained in crude bisβ-hydroxyethyl terephthalate to be subjected to molecular distillation to an extremely low level, and that it is a reason which purifying of bis-β-hydroxyethyl cannot be attained by conventionally known processes.

The present inventor has conducted intensive studies to overcome the above problem and has accomplished the present invention in the end.

The process of the present invention basically consists of four steps (1), (2), (3) and (4) as described above.

Crude terephthalic acid may be recovered terephthalic acid obtained by the liquid-phase air oxidation or nitric acid oxidation of paraxylene, recovered terephthalic acid obtained by the depolymerization of a polyester, for example, the depolymerization of polyethylene terephthalate and then acid neutralization, or terephthalic acid obtained by the hydrolysis of terephthalates. Or it may be a mixture of two or more out of these.

In the step (1), crude terephthalic acid is esterified with ethylene glycol and/or ethylene oxide to give a reaction product containing bis-β-hydroxyethyl terephthalate.

The esterification reaction of crude terephthalic acid with ethylene glycol itself is well known. This can be carried out by heating 1 mol of crude terephthalic acid and 1.1 to 2.0 mol of ethylene glycol at 220 to 265° C. in the presence of an esterification catalyst. The reaction can be carried out under normal pressure or increased pressure, for example, 0.1 to 0.3 MPa. The reaction time is 2.5 to 4.0 hours. The esterification catalyst is a Zn, Ca or Mg carboxylate, sodium alcoholate or the like.

The esterification reaction of crude terephthalic acid with ethylene oxide itself is also well known. This can be carried out by heating 1 part by weight of crude terephthalic acid and 0.5 to 0.7 part by weight of ethylene oxide at 170 to 190° C. in the presence of benzene and an esterification catalyst. The reaction is generally carried out under increased pressure, for example, 1.0 to 1.2 MPa. The reaction time is 1.5 to 2.5 hours. The esterification catalyst is triethylamine, for example.

In the present invention, the deionization step (2) which will be described hereinafter is carried out after the step (1). Before the step (2), the reaction product obtained in the step (1) can be depolymerized with ethylene glycol. In this case, the reaction product formed by this depolymerization is used as the reaction product used in the step (2).

In the present invention, the reaction product obtained in the step (1) is deionized to prepare a deionized solution of bis-β-hydroxyethyl terephthalate in the step (2). Before this deionization, the reaction product obtained in the step (1) may be mixed with ethylene glycol as required to prepare a solution containing bis-β-hydroxyethyl terephthalate as the main solute and ethylene glycol as the main solvent. When the concentration of the reaction product obtained in the step (1) is higher than a level suitable for deionization which is preferably 5 to 30 wt % of bis-β-hydroxyethyl terephthalate, it is preferred to control the concentration of the reaction product to an appropriate range by mixing ethylene glycol.

In the step (2), the solution is contacted to a cation exchanger and/or an anion exchanger. The cation exchanger or anion exchanger may be particulate, chain-like, fibrous or amorphous. For example, the solution can be contacted to a particulate ion exchanger by charging the ion exchanger into a column and let passing a solution composition through the column. The cation exchanger is preferably a cation exchange resin and the anion exchanger is preferably an anion exchange resin. Preferred examples of the cation exchange resin include what have —SO₃H, —COOH or —N(CH₂COOH)₂ as a cation exchange functional group. They may be used alone or combination. Commercially available cation exchange resin products include the SK series, PK series and WK series of Diaion (of Mitsubish Chemical Co., Ltd.), and the IR series and IRC series of Amberlite (of Rohm and Haas Japan Co., Ltd.). Since the ion exchange functional groups of these commercially available products are stabilize& as a salt such as a sodium salt, they are generally converted into the above free acid groups when in use. Examples of the anion exchange resin include what have groups represented by the following formulae as an anion exchange functional group.

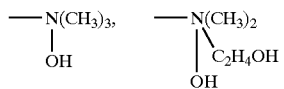

They may be used alone or in combination. Commercially available anion exchange resin products include the SA series, PA series and WA series of Diaion (of Mitsubishi Chemical Co., Ltd.), and the IRA series and IRAC900 series of Amberlite (of Rohm and Harse Japan Co., Ltd.). Since the ion exchange functional groups of these commercially available products are stabilized as what has a halogen anion and not a hydroxyl ion (OH⁻), they are generally converted into what have the above hydroxyl group anion when in use.

Gel type anion exchange resins are divided into a cracked type and a non-cracked type. The non-cracked type is preferred because the amount of adsorbed bis-β-hydroxyethyl terephthalate is small.

Further, porous, so-called microporous, ion exchange resins which are superior in physical durability and exchange adsorption speed to the gel type ion exchange resins may also be used.

Either one or both of the cation exchanger and the anion exchanger may be used. For example, when a solution composition containing a cation and an anion as impurities contains one of the ions in a much larger amount than the other ion and the content of the other ion is negligibly small, only an ion exchanger for removing the former ion may be used.

Generally speaking, both the cation exchanger and the anion exchanger are preferably used. In this case, the solution can be contacted to the cation exchanger and the anion exchanger simultaneously or sequentially. For example, simultaneous contact can be carried out by contacting the solution to a mixture of the cation exchange resin and the anion exchange resin and sequential contact can be carried out by contacting the solution to a column filled with the cation exchange resin and then a column filled with the anion exchange resin. Preferably, the solution is first contacted to the cation exchanger and then the anion exchanger sequentially.

The contact of the solution to the cation exchanger and the anion exchanger must be carried out at a temperature lower than the maximum use temperature of the ion exchange resins, preferably 20 to 120° C., more preferably 30 to 100° C., without the precipitation of bis-β-hydroxyethyl terephthalate crystals from the solvent.

The amount of bis-β-hydroxyethyl terephthalate as a solute is preferably 5 to 30 wt %, more preferably 8 to 25 wt %, particularly preferably 10 to 20 wt % to carry out a deionization step on a stable solution. Ethylene glycol used in the esterification step is preferably used as a solvent. The amount of ethylene glycol forming a solvent is preferably 70 to 95 wt %, more preferably 75 to 92 wt %, particularly preferably 80 to 90 wt %. The types and amounts of an anion and a cation contained in the solution change according to used substances such as crude terephthalic acid and do not limit the present invention. The anion is generally contained in an amount of 20 to 3,000 ppm and the cation is generally contained in an amount of 2,000 to 3,000 ppm in most cases.

Contact may be carried out under normal pressure, reduced pressure or increased pressure. It is needless to say that contact is carried out under conditions such as concentration, temperature and pressure for maintaining the solution in a solution state.

In the present invention, before the step (2) after the step (1), during the step (2) or before the step (3) after the step (2), an ethylene glycol solution containing bis-β-hydroxyethyl terephthalate is preferably decolorized one time or plural times. In this decolorization step, it is preferred that the solution may be contacted to a decolorant such as conventionally known active carbon and then solid-liquid separation may be made on the solution for decolorization. Decolorization is preferably carried out before ion exchanging because the mixing of ions from the decolorization step is prevented.

After the solution is contacted to the ion exchangers in the step (2), a deionized solution containing bis-β-hydroxyethyl terephthalate having a small ion content, that is, a total content of an anion and/or a cation as impurities of 50 ppm or less, preferably 40 ppm or less, based on bis-β-hydroxyethyl terephthalate is obtained.

In the step (3), substances having a boiling point lower than that of bis-β-hydroxyethyl terephthalate is distilled off from the thus obtained deionized solution containing bis-β-hydroxyethyl terephthalate. The temperature for distilling off the substances having a boiling point lower than that of bis-β-hydroxyethyl terephthalate is, for example, 170° C. or less, preferably 100 to 150° C. The pressure is preferably 40,000 Pa (300 mmHg) or less, more preferably 20,000 Pa (150 mmHg) or less, particularly preferably 20 Pa (0.15 mmHg) to 130 Pa (1 mmHg) as an absolute pressure.

This distillation is carried out until the content of ethylene glycol in the system becomes preferably 10 wt % or less, more preferably 5 wt % or less, particularly preferably 2 wt % or less. By distilling off ethylene glycol and diethylene glycol to that range, the substances having lower boiling point than that of bis-β-hydroxyethyl terephthalate are completely removed and the distillation residue (crude bis-β-hydroxyethyl terephthalate) which is concentrated to such an extent that the molecular distillation of the next step (4) can be advantageously carried out is obtained. There is such an advantage that at least some of other impurities which may be existent in small amounts are removed while the substances having a boiling point lower than that of bis-β-hydroxyethyl terephthalate are distilled off. The impurities include a third component such as cyclohexane dimethanol or diethylene glycol when crude terephthalic acid is derived from a polyester, particularly a copolyester.

In the present invention, crude bis-β-hydroxyethyl terephthalate obtained in the step (3) is subjected to molecular distillation in the step (4). The term "molecular distillation" as used herein means not equilibrium distillation or evaporation at a distillation temperature and pressure but non-equilibrium evaporation by which evaporated molecules do not return to the evaporation surface substantially but move to the condensation surface unilaterally. As for conditions for this molecular distillation step, the temperature is preferably in the range of 130 to 250° C., more preferably 160 to 220° C. and the pressure is preferably 300 Pa (2.25 mmHg) (absolute pressure) or less, more preferably 70 Pa (0.5 mmHg) (absolute pressure) or less. Further, the average residence time in this molecular distillation step is preferably about 2 hours or less, more preferably about 1.5 hours or less.

In the process of the present invention, bis-β-hydroxyethyl terephthalate is preferably recrystallized one time or plural times between the steps (2) and (3), between the steps (3) and (4), or after the step (4).

This recrystallization step may be carried out simultaneous with decolorization as required. The solvent suitable for use in the recrystallization step is ethylene glycol, for example. Stated further, ethylene glycol is preferably used as the solvent in all the steps.

Bis-β-hydroxyethyl terephthalate obtained herein has extremely high purity and a polyester obtained from this as a raw material can be used sufficiently for various purposes.

The following examples are provided for the purpose of further illustrating the present invention but are in no way to be taken as limiting.

EXAMPLES

Example 1

83 kg (0.5 kgmol) of a substance obtained by washing with water and drying a yellow tinted substance which contained crude terephthalic acid having 98.4% purity obtained by subjecting paraxylene to liquid-phase air oxidation, 1.2% of 4-carboxybenzaldehyde, 0.2% of paratoluylic acid, 0.1% of benzoic acid and 0.1% of ash and others to remove free acetic acid and 37.2 kg (0.6 kgmol) of ethylene glycol for industrial use were charged into a 150-liter reactor, an esterification reaction was carried out at 260° C. and $0.15 \times 10^3$ KPa for 4 hours, and by-produced water was distilled off.

Thereafter, 510 kg of ethylene glycol for industrial use and 0.5 kg of sodium methylate were added to depolymerize the above esterified product using refluxing condition at a temperature lower than the boiling point of ethylene glycol and normal pressure for 2 hours and maintained at 70±3° C. for 3 hours to crystallize an unreacted oligomer and separate it by filtration. The oligomer was decolorized by the adsorption of active carbon at 80±3° C. and then deionized with an anion-cation exchange mixed bed to obtain a treated solution having a total cation weight of 9.4 ppm and a total anion weight of 0 ppm after deionization. (2 parts of cation exchange resin (Amberlite® IR120BH(HG)) and 1 part of anion exchange resin (Amberlite® IRA96SB) are mixed and used with total amount of 320L, column=550Φ×1,500 mm, rate of the solution passing through the column=120 L/hr, space velocity (SV)=0.375 hr$^{-1}$).

The obtained solution (having still light yellow color) was transferred to a jacketed and stirrer equipped vessel for mixing and was cooled to 10° C. by circulating a brine in the jacket to precipitate bis-β-hydroxyethyl terephthalate crystals which were then obtained by a filter-press. The obtained crystals were heated at 85 to 90° C. to be molten and placed in a thin film evaporator to distill off the low-boiling substances together with the remaining ethylene glycol at 13.33 Pa and 150° C., and then bis-β-hydroxyethyl terephthalate was subjected to molecular distillation at a vacuum degree of 1.333 to 2.666 Pa and 200° C. to obtain 121.6 kg of high-purity bis-β-hydroxyethyl terephthalate. Other molecular distillation conditions and results-are shown in Table 1.

TABLE 1

| 1. | amount of solution treated with molecular distiller (kg) | 123.7 |
|---|---|---|
| 2. | treatment time of molecular distiller (minutes) | 68.3 |
| 3. | amount of recovered purified bis-β-hydroxyethyl terephthalate (kg) | 121.6 |
| 4. | recovery of purified bis-β-hydroxyethyl terephthalate (%) | 98.3 |
| 5. | amount of formed oligomer (kg) | 1.66 |
| 6. | formation rate of oligomer (%) | 1.34 |

The analytical results of the quality of the obtained bis-β-hydroxyethyl terephthalate are shown in Table 2.

TABLE 2

| 1. | optical density | <0.01 |
|---|---|---|
| 2. | acid value (KOH mg/g) | 0.38 |
| 3. | saponification value (KOH mg/g) | 440 |
| 4. | melting point (° C.) | 111.8 |
| 5. | whiteness | L = 98.9, a = −0.7, b = 1.1 |
| 6. | total cation weight (ppm) | 0.81 |
| 7. | total anion weight (ppm) | 0 |
| 8. | bis-β-hydroxyethyl terephthalate (wt %) | 97.99 |
| 9. | mono-β-hydroxyethyl terephthalate (wt %) | 1.27 |
| 10. | oligomer (wt %) | 0.74 |

The optical density in the above table is an index for the evaluation of the quality of bis-β-hydroxyethyl terephthalate and proportional to the content of a 10 colored product. It was obtained by measuring the absorbance of a 10% methanol solution at a wavelength of 380 μm and a cell length of 10 mm. The whiteness was measured with a color difference colorimeter and represented by L (brightness), a (redness) and b 15 (yellowness) of the Hunter method.

The low-boiling substances distilled off by the above thin film evaporator contained diethylene glycol and a slight amount of bis-β-hydroxyethyl terephthalate in addition to ethylene glycol and esters.

An oligomer having a low degree of polymerization, monohydroxyethyl terephthalate and ash were observed in the residue in the evaporator after high-purity bis-β-hydroxyethyl terephthalate was distilled out.

What is claimed is:

1. A process for producing high-purity bis-β-hydroxyethyl terephthalate by carrying out the following steps (1) to (4) in the mentioned order:

(1) the step of esterifying crude terephthalic acid with ethylene glycol and/or ethylene oxide to form a reaction product containing bis-β-hydroxyethyl terephthalate;

(2) the step of preparing a solution containing bis-β-hydroxyethyl terephthalate as the main solute and ethylene glycol as the main solvent by mixing the above reaction product obtained in the above step (1) with ethylene glycol as required and deionizing the solution to form a deionized solution of bis-β-hydroxyethyl terephthalate;

(3) the step of distilling off substances having a boiling point lower than that of bis-β-hydroxyethyl terephthalate from the above deionized solution obtained in the step (2) to form crude bis-β-hydroxyethyl terephthalate; and (4) the step of subjecting the crude bis-β-hydroxyethyl terephthalate obtained in the step (3) to molecular distillation to distill out bis-β-hydroxyethyl terephthalate.

2. The process of claim 1, wherein the step of depolymerizing the reaction product obtained in the step (1) with ethylene glycol is carried out between the above steps (1) and (2) and the reaction product formed in this depolymerization step is used as the reaction product in the step (2).

3. The process of claim 1, wherein an ethylene glycol solution containing bis-β-hydroxyethyl terephthalate is decolorized one time or plural times before the step (2) after the step (1), during the step (2), or before the step (3) after the step (2).

4. The process of claim 1, wherein bis-β-hydroxyethyl terephthalate is recrystallized one time or plural times between the steps (2) and (3), between the steps (3) and (4), or after the step (4).

5. The process of claim 1, wherein crude terephthalic acid in the step (1) is an oxidized product of paraxylene.

6. The process of claim 1, wherein crude terephthalic acid in the step (1) is a depolymerized product of polyethylene terephthalate.

7. The process of claim 1, wherein crude terephthalic acid in the step (1) is a product obtained by the alkali decomposition of polyethylene terephthalate and the subsequent acid neutralization.

8. The process of claim 1, wherein crude terephthalic acid in the step (1) is a hydrolyzed product of a terephthalate.

* * * * *

UNITED STATES PATENT AND TRADEMARK OFFICE
CERTIFICATE OF CORRECTION

PATENT NO. : 6,710,202 B2  
DATED : March 23, 2004  
INVENTOR(S) : Inada et al

Page 1 of 1

It is certified that error appears in the above-identified patent and that said Letters Patent is hereby corrected as shown below:

Column 7,  
Line 58, "380 µm" should read -- 380 mµ --

Signed and Sealed this

Twenty-ninth Day of June, 2004

JON W. DUDAS  
*Acting Director of the United States Patent and Trademark Office*